United States Patent
Schrier et al.

(10) Patent No.: US 6,458,363 B1
(45) Date of Patent: Oct. 1, 2002

(54) METHOD TO PRODUCE INACTIVATED W/O EMULSION ADJUVATED VACCINES

(75) Inventors: Carla Christina Schrier, Boxmeer (NL); Eric Onno Rijke, Boxmeer (NL)

(73) Assignee: Akzo Nobel N.V., Amhem (NL)

( * ) Notice: Subject to any disclaimer, the term of this patent is extended or adjusted under 35 U.S.C. 154(b) by 0 days.

(21) Appl. No.: 09/868,818

(22) PCT Filed: Dec. 15, 1999

(86) PCT No.: PCT/EP99/10178

§ 371 (c)(1),
(2), (4) Date: Jun. 21, 2001

(87) PCT Pub. No.: WO00/37101

PCT Pub. Date: Jun. 29, 2000

(30) Foreign Application Priority Data

Dec. 21, 1998 (EP) .............................................. 98204348

(51) Int. Cl.$^7$ ............................................. A61K 39/295
(52) U.S. Cl. ................. 424/204.1; 424/816; 435/235.1; 435/236; 435/810
(58) Field of Search ........................... 435/173.3, 235.1, 435/236, 810; 424/204.1, 816

(56) References Cited

FOREIGN PATENT DOCUMENTS

| EP | 0 838 222 A | 4/1998 |
|---|---|---|
| GB | 2 170 708 A | 8/1986 |

OTHER PUBLICATIONS

Thayer et al., Poultry Science, (Oct. 1983) 62 (10) Jul. 1991.*

* cited by examiner

*Primary Examiner*—Laurie Scheiner
(74) *Attorney, Agent, or Firm*—William P. Ramey III; William M. Blackstone

(57) ABSTRACT

The present invention is directed to a method to prepare an inactivated w/o emulsion adjuvated vaccine, wherein an aqueous solution comprising one or more inactivated angigens is mixed under mild conditions with a ready-made w/o emulsion. Preferably the vaccine is prepared just prior to vaccination. The aqueous solution and w/o emulsion are stirred or shaken by mechanical means or by hand. The present invention also relates to a kit of parts for use in a method according to the invention.

8 Claims, 1 Drawing Sheet

EFFECT OF ADDITION OF IB ANTIGEN TO GNE EMULSIONS IN CHICKENS

Fig.1

METHOD TO PRODUCE INACTIVATED W/O EMULSION ADJUVATED VACCINES

The present invention is related to inactivated vaccines and a method to produce said vaccines.

Vaccines have been widely used for the prophylaxis and treatment of infectious diseases in both animals and man. The vaccines used can be divided in two main categories: live vaccines and inactivated vaccines. Live vaccines make use of naturally occurring mild strains or attenuated strains of live pathogens. Inactivated vaccines comprise antigens constituting whole inactivated micro-organisms or specific components (subunits) of said micro-organisms. In case of the latter, two types of inactivated vaccine are distinguished: subunit vaccines in case of components that have been obtained via biochemical purification, or recombinant vaccines in case the isolated components of the microorganism have been prepared via recombinant technology.

Inactivated vaccines have the advantage over live vaccines in that this way of immunisation against pathogens has no risk of infection. The general problem perceived with the use of inactivated vaccines is their inability to raise an immune response that is sufficient for protection. As a consequence, inactivated vaccines are often combined with an adjuvant, i.e. a compound or composition that is capable to increase the general or specific immune response in the vaccinated subject. The administration of inactivated micro-organisms or components thereof and the adjuvant leads to a strong, effective and generally protective immune response. One of the most commonly used adjuvants is a water-in-oil (w/o) emulsion. W/o emulsions provide a two phase system for the vaccine: an aqueous phase in which the antigen can be dissolved or suspended and an oil phase in which the aqueous phase is dispersed as small droplets.

Inactivated vaccines that make use of a w/o emulsion as adjuvant are usually prepared by emulsifying an aqueous solution comprising the inactivated antigen, a suitable oil and emulsifying agents until a w/o emulsion is obtained in which the antigens are homogeneously distributed over the aqueous phase. The production of these inactivated w/o emulsion adjuvated vaccines takes considerable time and costs, but is generally regarded as necessary: only thorough emulsification of the antigen would lead to a homogeneous distribution of said antigen in the w/o emulsion. This is generally considered to be necessary for effectively stimulating the immune response. The emulsification process however is a highly energetic process carried out under vigorous process conditions including high temperatures and/or strong shear forces. For some antigens, these vigorous emulsification conditions can alter the structure or conformation of the antigen and as such reduce the efficacy of the resulting vaccine. Storage in emulsified form can decrease the stability of the antigen because the antigen is present in a dissolved or suspended state. Furthermore, during storage the chemical components that are present in the emulsion can reduce the stability of the antigen, as is the case for example with enveloped viruses: prolonged contact with the emulsifying agent destroys the viral envelope resulting in a decreased efficacy of the vaccine.

Surprisingly it was now found that inactivated, w/o emulsion adjuvated vaccines can be prepared by simply mixing of an aqueous solution comprising the inactivate,d antigen and a ready-made w/o emulsion, said mixing carried out under mild conditions. The vaccines thus obtained were found to be homogeneous compositions, which remained homogeneous for extended periods of time, despite the fact that the aqueous solution comprising the inactivated antigen had not been subjected as a whole to an emulsification process.

As already indicated emulsification is a highly energetic process in which an aqueous phase, an, emulsifying (surfactant) agent and a non-aqueous phase, preferably an oil phase, are mixed under vigorous process conditions. The mixing process according to the present invention however is carried out under extremely mild process conditions compared to the process conditions of the emulsification process, said mild conditions including low or no shear forces and ambient temperatures. Preferably the mixing process according to the present invention, is carried out by hand at ambient temperature.

Mixing of said aqueous antigen solution and said ready-made w/o emulsion according to the invention can be carried out by mere shaking, stirring or any other way of combining the two constituents without the excessive process parameters that are necessary for emulsification. Compared with the time needed for emulsification, mixing according to the invention can be carried out in a short time period. Preferably the mixing is achieved in a few seconds or minutes. More surprisingly, it was found that the mere shaking by hand of said aqueous solution and the already prepared w/o emulsion was sufficient to obtain a stable and homogeneous inactivated vaccine composition with an efficacy similar to an inactivated vaccine prepared according to a standard emulsification process.

The aqueous solution according to the invention comprises one or more inactivated antigens. An aqueous solution comprising two or more different inactivated antigens can be used in the method according to the invention to obtain multivalent inactivated vaccine emulsions.

The method of preparation according to the invention has several advantages over standard methods of preparation: it is easy to carry out, less time consuming and a more economical process. An important advantage of the method according to the present invention is the fact that the inactivated antigen is not exposed to the damaging shear forces and/or high temperatures that occur during the emulsification process: the chemical structure of the antigen is better preserved.

In a specific embodiment of method according to the invention the w/o emulsion adjuvated vaccine is prepared in the field prior to vaccination. The method provides a veterinarian a more flexible and adequate reaction upon field circumstances: in case of an outbreak the necessary inactivated antigens can be dissolved in an aqueous solution, mixed by hand with a suitable amount of a stable, ready-made w/o emulsion, and subsequently administered to the subject animals. Thus the method according to the invention provides for a quick and effective preparation of inactivated vaccine emulsions in the field just prior to use.

A further advantage of the method according to the invention is that in this way inactivated antigens which are normally not compatible, can be mixed together prior to vaccination to obtain a multivalent inactivated vaccine emulsion. Since the incompatible inactivated antigens are combined just prior to vaccination, they are only present in the emulsion for a short-lived period during which they cannot exert their adverse effect on each other.

Another advantage of the method according to the invention is that the inactivated antigens can be stored separately in dried form, preferably in lyophilised form, to prevent deterioration of the components during storage. The stability of the inactivated antigens declines much faster during storage in solution or suspension than in dried form. Just prior to vaccination the dried components are re-constituted with water into an aqueous solution. The dried vaccine components furthermore need less storage capacity than their corresponding solutions or suspensions.

Thus, the present invention provides for a method to prepare an inactivated, w/o emulsion adjuvated vaccine, wherein an aqueous solution comprising one or more inactivated antigens is mixed under mild conditions with a ready-made w/o emulsion. Preferably the aqueous solution and the w/o emulsion are stirred or shaken. The aqueous solution and the w/o emulsion can be mixed, preferably stirred or shaken, by mechanical means or by hand, more preferably by hand. The ready-made w/o emulsion may additionally comprise one or more antigens.

In a further embodiment the invention provides for a method to prepare an inactivated, w/o emulsion adjuvated vaccine, wherein an aqueous solution comprising one or more inactivated antigens is mixed with an already prepared w/o emulsion just prior to vaccination. Preferably the aqueous solution and the w/o emulsion are stirred or shaken, more preferably shaken. The aqueous solution preferably comprises a combination of inactivated antigens. The ready-made w/o emulsion may additionally comprise one or more antigens.

In another embodiment the invention provides for a kit of parts that can be used for the preparation of an inactivated, w/o emulsion adjuvated vaccine, said kit comprising at least one dosage of inactivated antigen and a separate dosage of a stable w/o emulsion. Preferably said kit comprises two or more dosages of inactivated antigen, each dosage constituting a different inactivated antigen. The inactivated antigen in a kit according to the invention is presented in the form of an aqueous solution or suspension or in a stable freeze-dried form. Preferably the antigen is presented in a stable, freeze dried form such as e.g. lyosphere, powder or tablet, which has to be dissolved in a small volume of water before use in a method according to the invention. In addition the separate dosage of w/o emulsion may comprise one or more antigens.

A kit according to the invention is suitable for use in the field and provides for tailor-made vaccines. Depending on the field circumstances, a proper selection of inactivated vaccines is dissolved in a small volume of water, stirred or shaken with a suitable amount of w/o emulsion and subsequently administered to the subjects. Thus a kit according to the present invention enables an adequate and quick reaction to an outbreak in the field.

A preferred kit according to the invention comprises inactivated IBDV antigens and optionally one or more inactivated antigens of chicken pathogens, preferably NDV and IBV.

For the purpose of the invention, the inactivated antigens are defined as immunogenic material derived from infectious micro-organisms (pathogens), which immunogenic material is non-replicative as opposed to live antigens. Inactivated antigens that are suitable for use in the method or kit according to the invention include inactivated whole micro-organisms of viral, bacterial or parasital origin, extracts of said micro-organisms or purified subunits of said micro-organisms. Examples of suitable micro-organisms include but are not limited to Newcastle Disease Virus (NDV), Infectious Bursal Disease Virus (IBDV), Infectious Bronchitis virus (IBV), *E. coli*, CM, Reo virus, coccidial agents and the like. The micro-organisms can be inactivated by chemical or physical means following conventional methods. Suitable chemical agents are for example formaldehyde, glutaraldehyde, β-propiolactone, ethyleneimine and derivatives. Suitable physical agents for inactivation of micro-organisms are for example UV radiation, γ-radiation, "heat-shock", and X-radiation. The inactivated antigens can also be isolated (recombinant) components or subunits or extracts of a pathogen, e.g. purified protein, protein-polysaccharide, protein-lipopolysaccharides, lipopolysaccharides and the like.

The inactivated antigens according to the invention may be produced by conventional methods known in the art including biochemical purification or recombinant DNA technology or may be purchased from commercial sources. In case of the latter, the inactivatede antigens are often present as a freeze-fried or lyophilised powder, tablet or lyosphere, and have to be dissolved in a small volume of water before use in a method according to the invention.

W/o emulsions that are suitable for use in a method according to the invention can be produced by methods known in the art or may be purchased commercially.

The oil component of the w/o emulsion will be present in an amount from 40% to 90% by weight, preferably 50% to 80% by weight. Especially preferred are w/o emulsions in which the oil component is present in an amount of 55% by weight.

The oil component of the w/o emulsion includes mineral oils such as Bayol® and Drakeol® and metabolizable oils. Suitable metabolizable oils are vegetable oils, fish oils, animal oils, tocopherol and tocopherol derivatives, and synthetically produced oils which can be metabolised and which are not toxic to the subject's body. Sources for vegetable oils include nuts, seeds, and grains. The most commonly available nut oil are peanut oil, soybean oil, coconut oil and olive oil. Seed oils include safflower oil, cottonseed oil, sunflower oil, sesame seed oil, and the like. Grain oil includes oil from cereal grains such as corn, wheat, oats, rye, rice, and the like. Fish oils include oil which can be readily recover led from fish, such as cod liver oil, shark liver oil, and the like. Suitable animal oils include whale liver oil. Synthetic oils include a number of branched chain oils that are synthesised biochemically in 5-carbon isoprene units and which are referred to as terpenoids. Squalene is a branched unsaturated terpenoid that is present in shark liver oil. Both squalene and its saturated analogue squalane are preferred oils and like the other fish oils are readily available from commercial sources or may be produced by methods known in the art.

The aqueous component of the w/o emulsion includes water, a buffer, saline, and the like.

W/o emulsions may be. prepared by conventional methods using emulsifying agents and/or emulsifying surfactant agents including Span 80, Span 85, Arlacel 80, Tween 80 and the like.

The particle size of the droplets of the dispersed phase is less than 20 $\mu$m, preferably less than 1 $\mu$m, more preferably less than 0.5 $\mu$m in diameter. Preferably the w/o emulsion according to the invention is a stable emulsion.

Optionally, the w/o emulsions according to the invention comprise one or more antigens.

The inactivated, w/o emulsion adjuvated vaccines thus prepared by the method according to the invention can be used to vaccinate animals and man against disease causing pathogens. The vaccines can be administered per oral or via parenteral routes such as for example subcutaneous (sc.) injection, intramusculair (im) injection, intraperitoneal (ip) injection. Other administration routes that are favoured are application via the respiratory tract, e.g. eye drops, nasal drops, aerosol spray.

The following examples are for illustration only and are not to be interpreted as a limitation of the scope of the invention.

LEGENDS TO THE FIGURES

FIG. 1: Effect of addition of inactivated IBV antigen to a w/o emulsion based on mineral oil in chickens (example 4).

EXAMPLES

Example 1

Addition of Inactivated Newcastle Disease (NDV) Antigen

Preparation of the vaccines: NDV antigen was grown on chicken eggs, harvested and inactivated (NDV antigen was concentrated 32× by ultracentrifugation) and used proportionally for the preparation of the vaccines: either 1 ml of concentrated inactivated NDV was added to before emulsification of the mineral oil (vaccines obtained this way are referred to as the "antigen-inside" formulation representing the prior art vaccines) or 1 ml of concentrated inactivated NDV was added to 500 ml of a ready-made mineral oil w/o emulsion and shaken by hand for one minute prior to administration (vaccine obtained in this way are referred to as "antigen-outside" formulations representing the invention). The ready-made mineral oil emulsion in some cases comprised an additional IBV antigen. Groups of 9 four week old female-SPF chickens were injected intramuscularly with 0.5 ml of the indicated vaccine formulation. Blood samples were taken at times indicated and antibody titers in serum were determined by means of the haemagglutination inhibition test (HI). As presented in table 1, the NDV "antigen-outside" vaccine formulation displayed similar antibody profiles as the "antigen-inside" vaccine formulation. The anti-IBV-antibody responses of the samples are presented in table 2, and no large differences were observed indicating that the addition of NDV antigen had no influence on the antibody response against the IBV antigen.

TABLE 1

| Vaccines | Formulation | Anti-NDV-antibody response* | | | |
|---|---|---|---|---|---|
| | | 3 wkpv | 6 wkpv | 9 wkpv | 12 wkpv |
| IBV | inside | 0.0 ± 0.0 | 0.0 ± 0.0 | 0.0 ± 0.0 | 0.0 ± 0.0 |
| NDV | inside | 7.9 ± 0.9 | 8.7 ± 0.9 | 8.3 ± 1.0 | 9.2 ± 1.0 |
| IBV + NDV | inside | 7.9 ± 0.8 | 8.6 ± 0.7 | 7.9 ± 1.0 | 8.8 ± 0.7 |
| NDV | outside | 8.3 ± 0.5 | 9.1 ± 0.6 | 7.6 ± 0.5 | 8.3 ± 0.7 |
| IBV + NDV | outside | 8.1 ± 0.3 | 8.1 ± 0.8 | 7.6 ± 1.0 | 8.0 ± 1.1 |
| Control | — | 0.0 ± 0.0 | 0.0 ± 0.0 | 0.0 ± 0.0 | 1.3 ± 2.1 |

*mean
$^2$log HI titer ± standard deviation
Antibody response of chickens against inactivated NDV after vaccination. Vaccines comprise one or more antigens in mineral oil w/o emulsion (example 1); "inside" = IBV or (IBV + inactivated NDV) antigen added before emulsification of mineral oil; "outside" = inactivated NDV antigen added to ready-made mineral oil w/o emulsion with IBV antigen or ready-made mineraloil w/o emulsion without IBV antigen; wkpv = weeks post vaccination; control = saline.

TABLE 2

| Vaccines | Formulation | Anti-IBV-antibody response* | | | |
|---|---|---|---|---|---|
| | | 3 wkpv | 6 wkpv | 9 wkpv | 12 wkpv |
| IBV | inside | 4.9 ± 1.2 | 6.9 ± 2.0 | 7.0 ± 1.1 | 7.2 ± 1.3 |
| NDV | inside | 4.0 ± 0.0 | 4.0 ± 0.0 | 3.9 ± 0.3 | 3.9 ± 0.3 |
| IBV + NDV | inside | 5.6 ± 1.2 | 7.4 ± 0.9 | 6.7 ± 0.9 | 7.8 ± 1.1 |
| NDV | outside | 4.0 ± 0.0 | 3.9 ± 0.3 | 4.0 ± 0.0 | 3.8 ± 0.5 |
| IBV/NDV | outside | 5.2 ± 1.7 | 6.4 ± 1.4 | 7.0 ± 1.3 | 7.0 ± 1.4 |
| Control | — | 4.0 ± 0.0 | 3.9 ± 1.2 | 3.8 ± 0.4 | 3.6 ± 0.7 |

*mean
$^2$log HI titer ± standard deviation
Antibody response of chickens against inactivated IBV after vaccination. Vaccines comprise one or more antigens in mineral oil w/o emulsion (example 1); "inside" = IBV or (IBV + inactivated NDV) antigen added before emulsification of mineral oil; "outside" = inactivated NDV antigen added to a ready-made mineral oil w/o emulsion with IBV antigens or a ready-made mineral oilw/o emulsion without IBV antigen; wkpv = weeks post vaccination; control = saline

Example 2

Addition of F11 Antigen

Preparation of the vaccines: F11 pilus protein derived from *E. coli* was used to prepare the vaccines similar to the procedure described above: either 1 ml of concentrated F11 antigen was added before emulsification of the mineral oil ("antigen-inside" formulation) or 1 ml of concentrated F11 antigen was added to 500 ml of emulsion and shaken by hand for one minute prior to administration ("antigen-outside" formulation). The ready-made mineral oil emulsion in some cases comprised additional IBV and NDV antigens. Groups of 10 four week old female SPF chickens were injected intramuscularly with the indicated vaccine formulation (10 μg F11 per dosis vaccine). Blood samples were taken at times indicated and antibody titers were determined in serum by means of an Elisa (incubation with F11 coated microtiter plates and chicken serum; incubation with anti-chicken Ig antibodies-enzyme conjugate). When F11 antigen was added to w/o emulsions without antigen or w/o emulsions comprising IBV+NDV antigens, no significant differences in antibody response against F11 were observed between the various groups (table 3). Moreover, addition of F11 to the emulsions comprising IBV and NDV antigens had no influence on the antibody response against either IBV or NDV (data not shown).

TABLE 3

| Vaccines | Formulation | Anti-F11-antibody response* | | | |
|---|---|---|---|---|---|
| | | 3 wkpv | 6 wkpv | 9 wkpv | 12 wkpv |
| IBV + NDV F11 | inside | 5.3 ± 0.7 | 6.0 ± 0.7 | 7.0 ± 0.8 | 7.4 ± 0.6 |
| F11 | inside | 10.7 ± 1.8 | 13.3 ± 2.8 | 12.6 ± 2.6 | 14.6 ± 1.9 |
| IBV/NDV/ F11 | inside | 8.7 ± 1.3 | 11.1 ± 1.6 | 11.7 ± 1.3 | 13.0 ± 2.1 |
| F11 | outside | 9.3 ± 1.4 | 12.2 ± 1.1 | 13.1 ± 1.7 | 14.9 ± 1.4 |
| IBV/NDV/ F11 | outside | 8.7 ± 2.2 | 11.8 ± 2.2 | 13.2 ± 1.8 | 13.2 ± 1.9 |
| control | — | 5.4 ± 0.7 | 6.3 ± 0.6 | 7.2 ± 0.8 | 7.5 ± 0.8 |

*mean
$^2$log Elisa titer ± standard deviation
Antibody response of chickens against F11 pilus protein after vaccination. Vaccines comprise one or more antigens in mineral oil w/o emulsion (example 2); "inside" = F11 and/or (IBV and NDV) antigen added before emulsification of mineral oil; "outside" = F11 antigen added to ready-made mineral oil w/o emulsion with IBV and NDV antigens or ready-made mineral oil w/o emulsion without IBV and NDV antigens;wkpv = weeks post vaccination; control = saline

Example 3

Addition of Inactivated Gumboro Disease Virus (IBDV)

Preparation of the vaccines: Various vaccines were prepared using different lots of inactivated IBDV antigens ($10^{7.3}$ TCID$_{50}$/ml) similar to the procedure described above: either 1 ml of concentrated inactivated IBDV antigen was added before emulsification of the mineral oil ("antigen-inside" formulation) or 1 ml of concentrated inactivated IBDV antigen was added to 500 ml of ready-made mineral oil w/o emulsion and shaken by hand for one minute prior to administration ("antigen-outside" formulation). Groups of 8 four week old female SPF chickens were injected intramuscularly with the indicated vaccine formulation. Blood samples were taken at times indicated and antibody titers were determined in serum by means of an Elisa (incubation with IBDV-coated microtiter plates and chicken serum; incubation with anti-chicken-Ig antibodies-enzyme conjugate). When concentrated inactivated IBDV was added to the emulsions (table 4), a significant higher antibody response at 3 and 6 weeks post vaccination (rapid response) was found in groups that received emulsions With IBDV "outside"-formulation compared to the antibody response in the groups that received corresponding emulsions with IBDV "inside" formulation. At later stages after vaccination no large differences were observed, indicating that in case of vaccination with IBDV "antigen-outside" formulations the antibody response was very rapid compared to vaccination with other "antigens-outside" formulations (see results of examples 1 and 2). It can also be concluded that the observed antibody response is not dependent on a particular antigen lot.

Example 4

Addition of Inactivated Infectious Bronchitis Virus (IBV)

Preparation of the vaccines: Vaccines were prepared with inactivated IBV antigens similar to the procedure described above: 10 or 100 ml non-concentrated inactivated IBV antigen were either added before emulsification of the mineral oil ("antigen-inside" formulation) or added to respectively 490 or 400 ml of ready-made mineral oil w/o emulsion and shaken by hand for 1 min prior to administration ("antigen-outside" formulation). Groups of 9 four week old female SPF chickens were injected intramuscularly with the indicated vaccine formulation. The addition of different volumes of inactivated IBV antigen to a mineral oil w/o emulsion resulted in significantly higher antibody responses at 3 weeks post vaccination (pv) compared with the antibody responses observed after vaccination with the "antigen-inside" formulations. At 6 and 12 weeks post vaccination no significant differences in response between the three groups were observed (FIG. 1).

TABLE 4

| Vaccines | Formu-lation | Anti-F11-antibody response* | | | |
|---|---|---|---|---|---|
| | | 3 wkpv | 6 wkpv | 9 wkpv | 12 wkpv |
| IBDV | inside | 5.4 ± 0.5 | 10.5 ± 1.8 | 12.0 ± 1.9 | 12.4 ± 1.7 |
| IBDV | inside | 5.3 ± 0.7 | 8.9 ± 2.0 | 10.1 ± 1.6 | 10.6 ± 1.0 |
| IBDV | inside | 5.7 ± 0.8 | 10.6 ± 2.3 | 11.3 ± 2.6 | 11.4 ± 2.1 |
| IBDV | inside | 6.0 ± 1.0 | 9.5 ± 2.0 | 11.3 ± 1.2 | 12.0 ± 1.0 |
| IBDV | inside | 6.5 ± 1.7 | 11.4 ± 1.1 | 12.3 ± 1.3 | 11.7 ± 1.6 |
| IBDV | inside | 7.2 ± 2.3 | 10.7 ± 2.7 | 12.0 ± 2.3 | 12.1 ± 2.0 |
| IBDV | inside | 5.8 ± 0.8 | 10.8 ± 1.6 | 11.5 ± 1.6 | 11.2 ± 1.8 |
| IBDV | inside | 5.4 ± 1.1 | 8.3 ± 2.0 | 10.3 ± 1.6 | 10.9 ± 1.6 |
| IBDV | outside | 8.3 ± 1.8 | 12.1 ± 1.1 | 12.8 ± 1.3 | 11.9 ± 1.4 |
| IBDV | outside | 7.9 ± 2.5 | 11.6 ± 1.3 | 12.0 ± 1.2 | 11.7 ± 1.3 |
| IBDV | outside | 7.8 ± 1.2 | 12.1 ± 1.3 | 12.4 ± 1.6 | 11.4 ± 2.1 |
| IBDV | outside | 10.4 ± 1.5 | 11.7 ± 1.0 | 11.6 ± 1.4 | 10.9 ± 1.6 |
| IBDV | outside | 9.1 ± 0.9 | 12.8 ± 1.1 | 13.3 ± 0.8 | 12.2 ± 1.0 |
| IBDV | outside | 8.4 ± 1.6 | 11.6 ± 1.3 | 12.7 ± 0.9 | 12.3 ± 0.6 |
| IBDV | outside | 7.6 ± 1.4 | 12.0 ± 1.7 | 12.7 ± 2.2 | 12.1 ± 1.5 |
| IBDV | outside | 7.5 ± 1.8 | 10.7 ± 1.3 | 11.3 ± 1.9 | 10.8 ± 2.1 |
| Control | — | 5.3 ± 0.5 | 5.0 ± 0.0 | 5.1 ± 0.3 | 5.1 ± 0.3 |

*mean
$^2$log Elisa titer ± standard deviation
Antibody response of chickens against IBDV after vaccination. Vaccines comprising the antigens in mineral oil w/o emulsion; "inside" = inactivated IBDV antigen added before emulsification of mineral oil; "outside" = inactivated IBDV antigen added to ready-made mineral w/o emulsion without antigens; wkpv = weeks post vaccination; control = saline.

Example 5

Storage of w/o Emulsions to Which Inactivated NDV was Added

Vaccines prepared according to example 1 were stored for 3 months at +4° C. before vaccination. The same procedure as described in Example 1 was carried out and the results are shown in table 5. No significant differences in antibody response were noted between vaccination with "antigen-outside" formulations and vaccination with "antigen-inside" formulations, indicating that even after storage w/o emulsions to which inactivated antigen was added after emulsification performed similar to those w/o emulsions to which the inactivated antigen was added before emulsification and that the homogeneity of the emulsion was not altered.

TABLE 5

| Vaccines | Formu-lation | Anti-F11-antibody response* | | | |
|---|---|---|---|---|---|
| | | 3 wkpv | 6 wkpv | 9 wkpv | 12 wkpv |
| NDV | inside | 7.4 ± 0.5 | 7.6 ± 0.5 | 7.6 ± 0.7 | 7.0 ± 0.9 |
| NDV | outside | 8.3 ± 0.5 | 8.6 ± 0.9 | 7.8 ± 0.8 | 7.1 ± 0.8 |
| IBV + NDV | inside | 8.0 ± 1.0 | 9.0 ± 1.2 | 8.4 ± 0.9 | 8.2 ± 1.0 |
| IBV + NDV | outside | 8.1 ± 0.8 | 8.7 ± 1.0 | 8.4 ± 1.0 | 7.4 ± 0.7 |
| Control | — | 0.0 ± 0.0 | 0.1 ± 0.3 | 0.0 ± 0.0 | 0.1 ± 0.3 |

*mean
$^2$log HI titer ± standard deviation
Antibody response of chickens against inactivated NDV after vaccination with vaccines. Vaccines comprise one or more antigens in mineral oil w/o emulsion and have been stored for 3 months at 4° C. before use in vaccination; "inside" = IBV or (IBV + inactivated NDV) antigen added before emulsification of mineral oil; "outside" = inactivated NDV antigen added to ready-made mineraloil w/o emulsion with IBV antigen or ready-made mineral oil w/o emulsion without IBV antigen; wkpv = weeks post vaccination; control = saline.

What is claimed is:

1. A method for preparing an inactivated, water-in-oil emulsion adjuvated vaccine, comprising mixing an aqueous solution comprising one or more inactivated antigens under mild conditions with a ready-made water-in-oil emulsion.

2. The method according to claim 1, wherein said aqueous solution and said ready-made water-in-oil emulsion are mixed just prior to vaccination.

3. The method according to claim 1, wherein said antigen comprises inactivated Infectious Bursal Disease Virus (IBDV) or immunogenic subunits thereof.

4. The method according to claim 1, wherein the ready-made water-in-oil emulsion comprises at least one antigen.

5. A kit of parts that can be used for the preparation of an inactivated water-in-oil emulsion adjuvated vaccine just prior to vaccination, said kit comprising at least one dosage of inactivated antigen and a separate dosage of water-in-oil emulsion.

6. The kit according to claim 5, comprising two or more dosages of inactivated antigen, each dosage constituting a different inactivated antigen.

7. The kit according to claim 5, wherein at least one of the inactivated antigens is inactivated IBDV antigen.

8. The kit according to claim 5, wherein the water-in-oil emulsion comprises at least one antigen.

\* \* \* \* \*

UNITED STATES PATENT AND TRADEMARK OFFICE
CERTIFICATE OF CORRECTION

PATENT NO.    : 6,458,363 B1
DATED         : October 1, 2002
INVENTOR(S)   : Schrier et al.

It is certified that error appears in the above-identified patent and that said Letters Patent is hereby corrected as shown below:

Column 7,
TABLE 4 should read -- Anti-IBDV-antibody response* --

Column 8,
TABLE 5 should read -- Anti-NDV-antibody-response* --

Signed and Sealed this

Twenty-eighth Day of January, 2003

JAMES E. ROGAN
*Director of the United States Patent and Trademark Office*